73-633 SR
10/27/81 XR 4,296,753

United States Patent [19]

Goudin

[11] 4,296,753

[45] Oct. 27, 1981

[54] SUPPORT FOR A TRANSDUCER FOR EMITTING AND/OR RECEIVING ULTRASONIC SIGNALS IN A GIVEN ANGULAR SECTOR

[75] Inventor: Robert Goudin, La Varenne-St-Hilaire, France

[73] Assignee: U.S. Philips Corporation, New York, N.Y.

[21] Appl. No.: 76,025

[22] Filed: Sep. 17, 1979

[30] Foreign Application Priority Data

Sep. 19, 1978 [FR] France ............................... 78 26771

[51] Int. Cl.[3] ............................................ A61B 10/00

[52] U.S. Cl. ....................................... 128/660; 73/633

[58] Field of Search ............................... 128/660–663, 128/1 R, 633, 666; 73/618, 633

[56] References Cited

U.S. PATENT DOCUMENTS 4,103,677 8/1978 Lansiart et al. ..................... 128/660

4,137,777 2/1979 Haverl et al. ....................... 128/660

4,185,502 1/1980 Frank ................................ 128/660

4,222,374 9/1980 Sampson et al. ................... 128/1 R

*Primary Examiner*—William E. Kamm

*Attorney, Agent, or Firm*—Thomas A. Briody; Robert T. Mayer; Jack E. Haken

[57] ABSTRACT

A support for a transducer for emitting and/or receiving ultrasonic signals in a given angular sector, comprising a series of substantially coaxial, loop-shaped elements which are axially arranged one behind the other. The first element can be arranged on a surface of an object to be examined, while the transducer is secured in the last element. Every two successive elements can pivot through a given angle with respect to each other. The total angular distance of the assembly formed by the elements at least equals the chosen angular sector. When the orientation of the transducer changes with respect to the surface, the distance between the transducer and the surface is not substantially varied.

5 Claims, 4 Drawing Figures

Figure 1A:
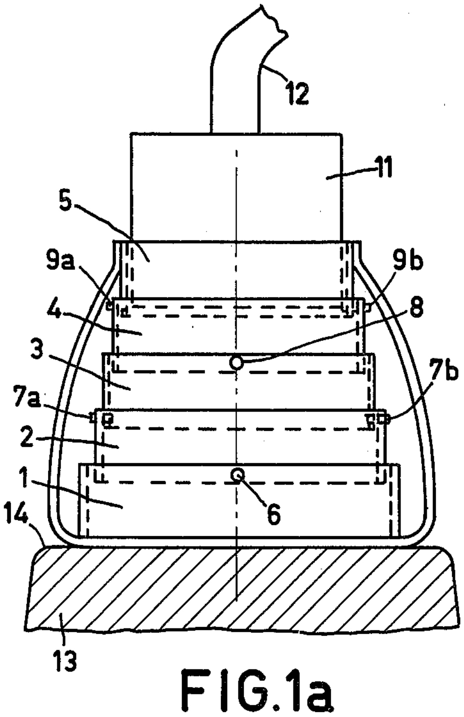

SUPPORT FOR A TRANSDUCER FOR EMITTING AND/OR RECEIVING ULTRASONIC SIGNALS IN A GIVEN ANGULAR SECTOR

The invention relates to a support for a transducer for emitting and/or receiving ultrasonic signals in a given angular sector with respect to a plane of an object to be examined, said support comprising a deformable bag which is filled with an ultrasonic coupling liquid. Medical examination of an organ or of an area of the human body is often performed by means of an echograph of the B-type, provided with an ultrasonic transducer which can operate in the focussing mode. The transducer is then accommodated at the end of a swivel arm whose movement, desired by the operator is followed by suitable electronic circuits, thus controlling the scan of a display screen. Focussing is obtained, for example, when the transducer comprises a number of concentric rings which are activated at a suitable phase difference with respect to each other. For proper focussing it is necessary for all rings to participate in the emission or reception of a signal; this is the case only if the transducer is situated at an adequate distance from the circumference of the surface of the object to be examined, i.e. generally at an adequate distance from the skin of the patient. However when the transducer is situated further from the skin of the patient, suitable coupling between the transducer and the skin must be provided in order to ensure suitable transmission of the ultrasonic pulses.

This coupling is realized by means of a deformable, sealed bag which is filled with a coupling liquid (usually water) and which is positioned against the skin of the patient; the transducer itself is pressed against this deformable bag so that the patient and the transducer are situated one on each side of said bag. However, for an effective examination of the complete object, it should be possible to orient the transducer in a given angular sector. As a result of these movements, substantial deformation of the bag occurs, resulting in a variation of the distance between the transducer and the skin of the patient; this variation may have an adverse effect on the efficiency of the focussing.

The invention has for its object to provide a support which enables orientation of the transducer while maintaining a substantially constant distance between the transducer and the surface of the object to be examined.

To this end, the support in accordance with the invention is characterized in that the support also comprises a series of substantially coaxial loop-shaped elements which are arranged axially one behind the other and the first one of which is adapted to be arranged against the surface of the object, the last element of the series being adapted for fixation of the transducer, the elements which are situated between the first element and the last element being each time pivotably connected to the preceding element and to the next element, so that the total angular rotation which can be realized between the last element and the first element at least equals the desired angular sector.

Preferably, the loop-shaped elements are formed by rotation-symmetrical rings, the pivot axis between two successive rings coinciding approximately with a centre line of each of said rings. These successive rings may exhibit a decreasing diameter, the diameter of the first ring being the largest and that of the last ring being the smallest. As a result, the rings fit one into the other, so that the construction of the pivots is simplified and the risk of the ultrasonic beam being incident on the internal surface of the rings, which would give rise to echo signals without useful effect, is eliminated.

In a preferred embodiment in accordance with the invention, the loop-shaped elements are formed by the turns of a helical spring, the length and the rigidity of which are such that the spring can be bent around its central position at least enough to realize the desired angular distance.

The invention will be described in detail hereinafter with reference to a drawing.

Figure 1B:
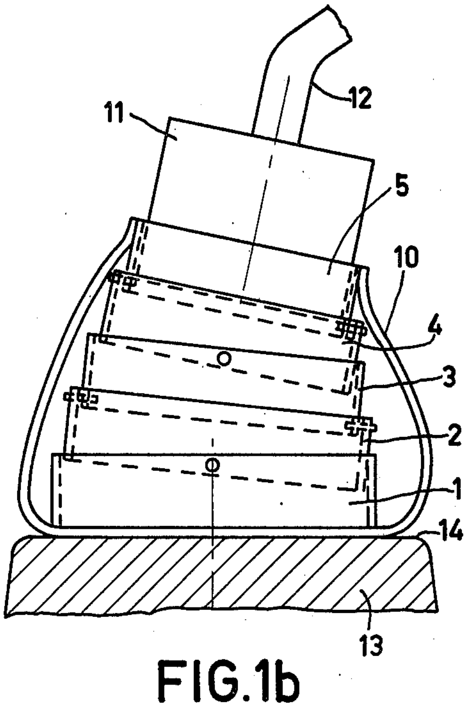
Figure 2A:
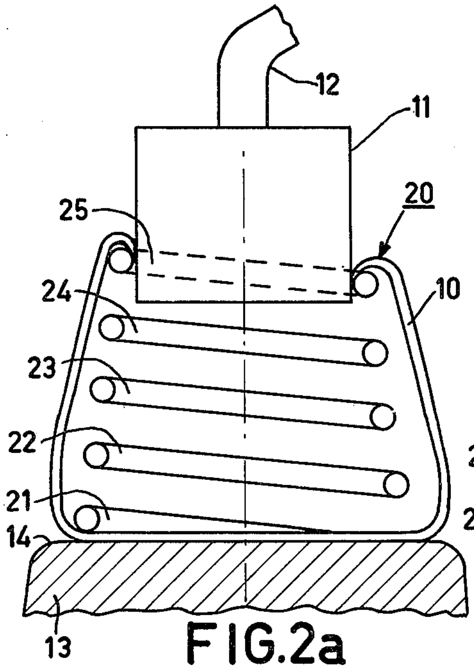
Figure 2B:
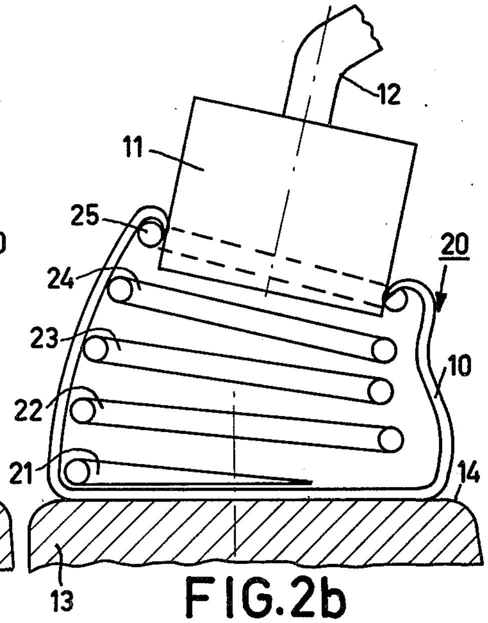

FIGS. 1*a* and 1*b* show a first embodiment of the support in accordance with the invention in the central position and in an extreme position, respectively, and FIGS. 2*a* and 2*b* similarly illustrate a second embodiment of a support in accordance with the invention.

The support shown n the FIGS. 1*a* and 1*b* comprises five rotation-symmetrical rings 1, 2, 3, 4 and 5. The internal diameter of each ring i is slightly larger than the external diameter of the next ring i+1, the first ring 1 being the largest ring and the last ring 5 being the smallest ring. The rings thus more or less fit one into the other.

In the zone where the internal surface of the ring 1 is situated opposite the external surface of the ring 2 both rings comprise two trunnions which form a pivot 6 which coincides with a centre line of each of the two rings. Thus, the rings 1 and 2 can pivot with respect to each other over an angular distance which is limited in that the side face of the ring 1 abuts against the external surface of the ring 2. Similarly, the pivots 7, 8 and 9 are formed each time by two trunnions for realizing the pivotable joints between the rings 2, 3 and 3, 4 and 4, 5, respectively. When the support is in its central position, i.e. in the position shown in FIG. 1*a* in which the rings 1 to 5 are parallel, the pivots 6 and 9 occupy angular positions which have been shifted through 90° with respect to each other. The pivots 6 and 8 are then parallel, whilst the pivots 7 and 9, also being mutually parallel, extend perpendicularly to said pivots 6 and 8.

Therefore, the trunnions 7*a* and 7*b* and the trunnions 9*a* and 9*b* which form the pivots 7 and 9, respectively, are visible in the Figure.

The support furthermore comprises a deformable sealed bag 10 which encloses the rings and which is filled with a coupling liquid in order to enable propagation of the ultrasonic pulses emitted by a transducer 11. The transducer 11 is arranged in the last ring 5, for example, by clamping it into this ring. The transducer 11 is connected, via a cable 12, to an electronic device (not shown). On the side of the ring 5, the bag 10 is fixed to the outer surface of the ring by means of an adhesive, whilst at the side of the ring 1 the bag is similarly fixed to the external side face of this ring.

During examination of an object 13, for example, a patient, the first ring 1 is pressed against a surface 14 of this object, in this case the skin of the patient. At the other end of the support, the operator can orient the transducer 11 so that it covers the entire angular sector in which the organ or area to be examined is situated.

During these orientation manipulations, the operator has the certainty that, thanks to the characteristics of the device used, no substantial deformation of the coupling bag 10 occurs and also no noticeable variation of the distance between the transducer and the surface 14.

In a second embodiment which is to be described with reference to the FIGS. 2*a* and 2*b*, the support comprises a helical spring 20, the successive turns 21 to 25 of which perform the function of loop-shaped elements which are pivotably interconnected. The transducer 11 is clamped in the last turn 25. A sealed deformable bag 10 which is filled with an ultrasonic coupling liquid is clamped at one end, together with the transducer 11, in the last turn 25 of the spring 20.

During examination of a patient 13, the first turn 21 is arranged against the skin 14 of the patient. On the other side of the support, the operator can orient the transducer 11 by bending the helical spring on either side of the neutral position of the spring. The distance between the transducer and the skin is determined substantially by the neutral length of the spring. The value of the sector angle in which the transducer can be oriented by the bending of the spring is obtained by imparting the desired rigidity to the spring.

The two embodiments of the support described above are simple, occupy little space, can be handled very well and offer the certainty that a sufficiently constant distance is maintained between the transducer and the surface of the object during the orientation of the transducer or after displacement of this transducer.

In the description of the support shown in the FIGS. 1*a* and 1*b*, the successive pivots of the rings have been shifted through 90° with respect to each other; this simple value is stated merely by way of example. Other angular values may also be chosen, for example, an angle of 360° divided by the number of pivots (i.e. the number of rings minus (1). In this case the circumference which limits the orientation sector of the transducer no longer has a pyramidal shape with a square cross-section as in the case of the first embodiment of the support, and also no longer has the substantially conical shape like in the second embodiment; it is pyramidal with a polygonal cross-section, the number of sides of the polygon thus defined being equal to the number of pivots.

What is claimed is:

1. A support for a transducer for emitting and/or receiving ultrasound signals in a given angular sector with respect to a plane at the surface of an object, comprising:

a series of rotationally symmetrical, coaxial rings which includes a first ring, one or more intermediate rings, and a last ring, disposed one behind another along a line which connects the transducer with the surface of the object, the first ring being adapted for placement adjacent the surface of the object and the last ring being adapted for attachment to the transducer, the first and each succeeding intermediate ring in the series being pivotably connected to the following ring in the series so that the transducer can achieve a total angular rotation with respect to the first ring which at least equals the given angular sector and so that the distance between the transducer and the plane remains substantially constant as the transducer is rotated through that sector;

a deformable, liquid-tight bag enclosing the rings; and coupling liquid means which fill the bag and surrounds the rings for coupling ultrasound signals from the transducer to the object.

2. The support of claim 1 wherein each ring is pivotable with respect to the next in the series about an axis which is substantially coincident with diameters of each of said rings, the successive pivot axes being disposed one behind another along the line which connects the transducer with the surface of the object.

3. A support as defined in claim 2 wherein each successive pivot axis in the series is disposed at an angle with respect to the preceding pivot axis in the series, the angles between all successive pivot axes in the series being equal.

4. The support as claimed in claim 3 wherein the angle between successive pivot axes in the series is 90°.

5. A support as claimed in any of the proceeding claims wherein each ring in the series has a smaller diameter than the preceding ring in the series, the diameter of the first ring being largest and the diameter of the last ring being smallest.

* * * * *